US008821905B2

(12) United States Patent
Watanabe

(10) Patent No.: US 8,821,905 B2
(45) Date of Patent: Sep. 2, 2014

(54) OIL-IN-WATER EMULSIFIED COMPOSITION

(75) Inventor: Takumi Watanabe, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 13/877,350

(22) PCT Filed: Oct. 4, 2011

(86) PCT No.: PCT/JP2011/072859
§ 371 (c)(1),
(2), (4) Date: Apr. 2, 2013

(87) PCT Pub. No.: WO2012/070315
PCT Pub. Date: May 31, 2012

(65) Prior Publication Data
US 2013/0189335 A1    Jul. 25, 2013

(30) Foreign Application Priority Data

Nov. 26, 2010  (JP) .................................. 2010-263572
Sep. 26, 2011  (JP) .................................. 2011-209211

(51) Int. Cl.
| | | |
|---|---|---|
| *A61K 8/02* | (2006.01) | |
| *A61Q 19/00* | (2006.01) | |
| *A61K 8/34* | (2006.01) | |
| *A61K 8/86* | (2006.01) | |
| *A61K 8/44* | (2006.01) | |
| *A61K 8/36* | (2006.01) | |
| *A61K 8/81* | (2006.01) | |
| *A61K 8/06* | (2006.01) | |
| *A61K 8/37* | (2006.01) | |
| *A61K 8/891* | (2006.01) | |
| *A61K 8/67* | (2006.01) | |

(52) U.S. Cl.
CPC ................ *A61K 8/062* (2013.01); *A61Q 19/00* (2013.01); *A61K 8/342* (2013.01); *A61K 8/86* (2013.01); *A61K 8/442* (2013.01); *A61K 8/361* (2013.01); *A61K 8/8111* (2013.01); *A61K 8/37* (2013.01); *A61K 8/891* (2013.01); *A61K 2800/21* (2013.01); *A61K 8/676* (2013.01)
USPC .............................. 424/401; 514/162; 514/27

(58) Field of Classification Search
None
See application file for complete search history.

(56) References Cited

U.S. PATENT DOCUMENTS

| | | | | |
|---|---|---|---|---|
| 6,150,425 A | * | 11/2000 | Sekine et al. ................... | 516/22 |
| 8,242,169 B2 | * | 8/2012 | Yoneda et al. ................. | 514/474 |
| 2013/0005835 A1 | * | 1/2013 | Uyama et al. .................. | 514/784 |

FOREIGN PATENT DOCUMENTS

| | | | |
|---|---|---|---|
| JP | H07-267814 A | | 10/1995 |
| JP | 2352919 | * | 9/1997 |
| JP | H09-235219 A | | 9/1997 |
| JP | H09-301847 A | | 11/1997 |
| JP | 3398171 B2 | | 4/2003 |
| JP | 2006-327952 A | | 12/2006 |
| JP | 2007-009199 A | | 1/2007 |
| JP | 2008-247866 A | | 10/2008 |
| JP | 2009-196980 A | | 9/2009 |

OTHER PUBLICATIONS

Japan Patent Office, "Notification of Reasons for Refusal," issued in JP 2011-209211 to which PCT/JP2011/072859 claims priority, dispatched on Jun. 22, 2012.
Japan Patent Office, "Notification of Reasons for Refusal," issued in JP 2011-209211 to which PCT/JP2011/072859 claims priority, dispatched on Dec. 12, 2011.
The International Bureau of WIPO, International Preliminary Report on Patentability, mailed in PCT/JP2011/072859 on Dec. 20, 2011; English translation mailed on Jun. 20, 2013.

* cited by examiner

*Primary Examiner* — Robert A Wax
*Assistant Examiner* — Danah Al-Awadi

(57) ABSTRACT

The present invention provides an oil-in-water emulsified composition comprising the following ingredients (A)-(G) characterized by miniaturization of the emulsified particles by means of high pressure emulsification:
(A) salt type drug
(B) hydrophilic nonionic surfactant
(C) N-long chain acyl acidic amino acid mono salt
(D) two or more types of higher fatty acids and alkali that constitutes higher fatty acid soap
(E) higher alcohol
(F) oil component
(G) water.
The object of the present invention is to provide an oil-in-water emulsified composition prepared by miniaturizing emulsified particles by means of a high pressure emulsification method, said composition being superior in terms of emulsification stability such that electrolyte salt type drugs can be stably blended in.

21 Claims, No Drawings

OIL-IN-WATER EMULSIFIED COMPOSITION

CROSS-REFERENCE TO RELATED APPLICATIONS IONS

This patent application is a U.S. national stage application under 35 U.S.C. §371 of International Patent Application No. PCT/JP2011/072859 filed on Oct. 4, 2011, which claims the benefit of foreign priority to Japanese Patent Application No. JP 2010-263572 filed on Nov. 26, 2010, and to Japanese Patent Application No, JP 2011-2019211 filed on Sep. 26, 2011, the disclosures of all of which are hereby incorporated by reference in their entireties. The International Application was published in Japanese on May 31, 2012, as International Publication No. WO 2012/070315 A1 under PCT Article 21(2).

TECHNICAL FIELD

The present invention relates to an oil-in-water emulsified composition. More specifically, it relates to an oil-in-water emulsified composition prepared by miniaturizing emulsified particles with a high pressure emulsification method, into which a salt-type drug can be stably blended, and a cosmetic utilizing thereof.

BACKGROUND ART

Recently, high function skin cosmetics having humectant actions, whitening actions, antioxidation actions, etc. are desired and the development thereof is desired. Therefore, for emulsified compositions which constitute skin cosmetics, for the purpose of manifesting the target high function, pH adjustment, thickening, etc., there are many cases where electrolytes such as plant extracts, organic acids and salts thereof including citric acid, ascorbic acid, and 4-methoxysalycilic acid are blended in as salt type drugs.

However, there is an essential problem with emulsified compositions in that the addition of an electrolyte decreases their stability over time and over varying temperatures. Particularly, the stability of low-viscosity oil-in-water emulsified compositions having aqueous solution-like physical properties dramatically worsens with the addition of a salt type drug consisting of electrolytes.

Such destabilization of emulsified compositions by the addition of electrolytes is also described in Patent Document 1, Non-Patent Document 1, Non-Patent Document 2, etc.

On the other hand, as examples of oil-in-water emulsified compositions prepared by miniaturizing emulsified particles by means of high pressure emulsification, Patent Documents 2-4 disclose oil-in-water emulsified compositions having aqueous solution-like low viscosity physical properties and also a cream-like texture during use. Patent Documents 2 and 3 are basically technologies using higher fatty acid soaps and Patent Document 4 is basically a technology using N-long chain acyl acidic amino acid mono salts.

However, the oil-in-water emulsified compositions of Patent Documents 2-4 have a relatively narrow range of selection in terms of combinations of surfactants and oil components as well as their blend ratios that can provide stable emulsified compositions. Therefore, it is not necessarily easy to stabilize said emulsified compositions when desired amounts of various salt type drugs are blended in: in many cases it is with difficulty.

PRIOR ART DOCUMENTS

Patent Documents

Patent Document 1: Japanese Patent No. 4406498
Patent Document 2: Japanese Patent No. 3398171
Patent Document 3: JP H7-267814 A
Patent Document 4: JP H9-301947 A
Non-Patent Document 1: "Bunsan, Nyukakei no Kagaku (Chemistry of Dispersed, Emulsified Systems)" by Fumio Kitahara and Kunio Furusawa, Kogaku Tosho, 1979, p 242
Non-Patent Document 2: "Keshohin Handbook (Cosmetics Handbook)" by Yoshiko Kurata, Takehito Tabata, Noriyuki Uchino, Toshio Onuma, and Hiroaki Tamura, Nikko Chemicals, 1995, p 201

OUTLINE OF THE INVENTION

Problem that the Present Invention Aims to Solve

The inventors took the above mentioned viewpoints in consideration and conducted earnest research in order to obtain an oil-in-water emulsified composition prepared by miniaturizing emulsified particles by means of the high pressure emulsification method, which composition being superior in terms of emulsification stability such that electrolyte salt type drugs can be stably blended in, and discovered that an oil-in-water emulsified composition consisting, as essential ingredients, of (A) salt type drug, (B) hydrophilic nonionic surfactant, (C) N-long chain acyl acidic amino acid mono salt, (D) two or more types of higher fatty acids and alkali that constitute higher fatty acid soap, (E) higher alcohol, (F) oil component, and (G) water can stably contain (A) salt type drug and manifests a superior effect in terms of emulsification stability, thus completing the present invention.

The object of the present invention is to provide an oil-in-water emulsified composition prepared by miniaturizing emulsified particles by means of the high pressure emulsification method, said composition being superior in terms of emulsification stability such that electrolyte salt type drugs can be stably blended in.

Means to Solve the Problem

That is, the present invention provides an oil-in-water emulsified composition comprising the following ingredients (A)-(G) characterized by miniaturization of the emulsified particles by means of high pressure emulsification:
(A) salt type drug
(B) hydrophilic nonionic surfactant
(C) N-long chain acyl acidic amino acid mono salt
(D) two or more types of higher fatty acids and alkali that constitutes higher fatty acid soap
(E) higher alcohol
(F) oil component
(G) water.

Also, the present invention provides a cosmetic characteristically comprising the aforementioned oil-in-water emulsified composition.

Effects of the Invention

The present invention can provide an oil-in-water emulsified composition prepared by miniaturizing emulsified particles by means of the high pressure emulsification method, said composition being superior in terms of emulsification stability such that electrolyte salt type drugs can be stably blended in.

THE EMBODIMENTS OF THE PRESENT INVENTION

The present invention is described in detail below.

"(A) Salt Type Drug"

The salt type drug blended into the present invention is an electrolyte and the addition of such an ingredient in many cases worsens the stability over time of the oil-in-water emulsified composition. However, in the present invention, even when a salt type drug is blended in, said emulsified composition will have excellent stability over time.

Specific examples of the salt type drug include salts of alkoxysalicylic acid and derivatives thereof: salts of L-ascorbic acid, L-ascorbic acid phosphoric ester, L-ascorbic acid-2-sulfuric ester, and L-ascorbic acid-2-glucoside and derivatives thereof; alkali metal salts or alkali earth metal salts such as sodium salt, potassium salt, or calcium salt, or ammonium salts or amino acid salts, of 4-methoxysalicylic acid; and potassium salts and ammonium salts of glycyrrhizic acid. The salt type drug resides in the water phase of the oil-in-water emulsified composition and is an ingredient that helps manifest the target function.

The blend ratio of the salt type drug is preferably 0.01-5 wt %, more preferably 0.5-3 wt %, most preferably 1-3 wt % relative to the total amount of the oil-in-water emulsified composition.

"(B) Hydrophilic Nonionic Surfactant"

In the present invention, the hydrophilic nonionic surfactant is an ingredient that acts as an emulsifier. Selection of the hydrophilic nonionic surfactant used in the present invention is not limited in particular: it is preferable to use a POE alkyl ether type nonionic surfactant; specifically, it is preferable to use one, two or more selected from POE (20) cetyl ether (EMALEX 120 from Nihon Emulsion), POE (25) cetyl ether (EMALEX 125 from Nihon Emulsion), POE (30) cetyl ether (EMALEX 130 from Nihon Emulsion), POE (30) behenyl ether (Nikkol BB-30 from Nikko Chemicals), and POE (20) behenyl ether (Nikkol BB-20 from Nikko Chemicals).

The blend ratio of the hydrophilic nonionic surfactant is preferably 0.01-1 wt %, more preferably 0.2-0.5 wt %, most preferably 0.3-0.4 wt % relative to the total amount of the oil-in-water emulsified composition.

"(C) N-long Chain Acyl Acidic Amino Acid Mono Salt"

In the present invention, an N-long chain acyl acidic amino acid mono salt is an ingredient that acts as an emulsifier. Selection of the N-long chain acyl acidic amino acid mono salt used in the present invention is not limited in particular; it is preferable to use one, two or more from sodium stearoyl glutamate (Amisoft HS-11P (F) from Ajinomoto), sodium lauroyl glutamate (Amisoft LS-11 from Ajinomoto), potassium myristoyl glutamate (Amisoft MK-11 from Ajinomoto), sodium myristoyl glutamate (Amisoft MS-11 from Ajinomoto), and such.

The blend ratio of the N-long chain acyl acidic amino acid mono salt is preferably 0.01-1 wt %, more preferably 0.2-0.5 wt %, most preferably 0.3-0.4 wt % relative to the total amount of the oil-in-water emulsified composition.

"(D) Two or More Types of Higher Fatty Acids and Alkali that Constitutes Higher Fatty Acid Soap"

In the present invention, two or more types of higher fatty acids and alkali that constitutes a higher fatty acid soap of said higher fatty acids are blended in. That is, in the formulation of the present invention, two or more types of higher fatty acids and alkali must be blended in and neutralized to form two or more types of higher fatty acid soaps having different types of higher fatty acids. Also, rather than separately blending in the higher fatty acids and alkali in the formulation, it is possible to blend in a higher fatty acid soap composed of two or more types of higher fatty acids.

The two or more types of higher fatty acid soaps from different types of higher fatty acid in the present invention act as emulsifiers in the same manner as the aforementioned ingredients (B) and (C).

Selection of the higher fatty acids used in the present invention is not limited in particular: specifically, it is preferable to use one, two or more from lauric acid, myristic acid, palmitic acid, stearic acid, behenic acid, isostearic acid, etc.

Selection of the alkali used in the present invention is not limited in particular: it is particularly preferable to use KOH.

For the two or more types of higher fatty acid soaps, particularly preferable are potassium stearate soap and potassium behenate soap.

The blend ratio of the higher fatty acid, as a total of two or more types, is preferably 0.1-5 wt %, more preferably 0.5-2 wt %, most preferably 0.8-1.2 wt % relative to the total amount of the oil-in-water emulsified composition.

The blend ratio of the alkali in mole number units is preferably 60% or more of the mole number of the two or more types of higher fatty acids; it is preferably 0.02-1.6 wt %, more preferably 0.01-0.6 wt %, most preferably 0.15-0.38 wt % relative to the total amount of the oil-in-water emulsified composition.

"(E) Higher Alcohol"

The higher alcohol used in the present invention is an ingredient that constitutes the oil phase of the oil-in-water emulsified composition and its selection is not limited in particular; specifically, it is preferable to use one, two or more from cetyl alcohol, stearyl alcohol, behenyl alcohol, myristyl alcohol, oleyl alcohol, cetostearyl alcohol, batyl alcohol, and isostearyl alcohol.

The blend ratio of the higher alcohol is preferably 0.1-5 wt %, more preferably 1-3 wt %, most preferably 1.5-2 wt % relative to the total amount of the oil-in-water emulsified composition.

"(F) Oil Component"

The oil component used in the present invention is an ingredient that constitutes the oil phase of the oil-in-water emulsified composition and its selection is not limited in particular.

Specific examples include liquid fats and oils such as avocado oil, tsubaki oil, turtle fatty acid, macadamia nut oil, corn oil, mink oil, olive oil, rapeseed oil, egg yolk oil, sesame oil, persic oil, wheat germ oil, sasanqua oil, castor oil, linseed oil, safflower oil, cotton seed oil, evening primrose oil, perilla oil, soybean oil, peanut oil, tea see oil, Japanese nutmeg oil, rice bran oil, Chinese gimlet oil, Japanese gimlet oil, jojoba oil, germ oil, and triglycerin, glycerin trioctanoate, and glycerin triisopalmitate;

solid fats and oils such as cacoa butter, coconut oil, hydrogenated coconut oil, palm oil, palm kernel oil, Japanese core wax nucleus oil, hydrogenated oil, Japanese core wax, and hydrogenated castor oil;

waxes such as beeswax, candelilla wax, cotton wax, carnauba wax, bayberry wax, tree wax, montan wax, bran wax, lanolin, kapok wax, lanolin acetate, liquid lanolin, sugar can wax, lanolin fatty acid isopropyl ester, hexyl laurate, reduced lanolin, jojoba wax, hard lanolin, shellac wax, POE lanolin alcohol ether, POE lanolin alcohol acetate, lanolin fatty acid polyethylene glycol, and POE hydrogenated lanolin ethyl alcohol ether;

hydrocarbon oils such as liquid paraffin, α-olefin oligomer, ozocerite, squalene, pristane, paraffin, ceresin, squalane, petrolatum, and microcrystalline wax;

silicone oils such as methylpolysiloxane, methylphenylpolysiloxane, and amino-modified silicone;

and synthetic ester oils such as isopropyl myristate, cetyl octanoate, octyl dodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di(2-ethylhexanoate), dipentaerythritol fatty acid ester, n-alkylene glycol monoisostearate, neopentyl glycol dicaprate, diisostearyl malate, glyceryl di-2-heptylundecanoate, trimethylolpropane tri-2-ethylhexylate, trimethylolpropane triisostearate, pentaerythritol tetra-2-ethylhexylate, glycerin tri-2-ethylhexylate, trimethylolpropane triisostearate, cetyl 2-ethyl hexanoate, 2-ethylhexyl palmitate, glycerin trimyristate, tri-2-heptyl undecanoic acid glyceride, castor oil fatty acid methyl ester, oleyl oleate, cetostearyl alcohol, acetoglyceride, 2-heptylundecyl palmitate, diisopropyl adipate, 2-octyldodecyl N-lauroyl-L-glutamate, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, ethyl acetate, butyl acetate, amyl acetate, and triethyl citrate; one, two or more of these oil components can be used.

Particularly preferable oil components in the present invention are liquid paraffin, α-olefin oligomer, squalane, petrolatum methylpolysiloxane, and cetyl octanoate.

The blend ratio of the oil component is determined as appropriate: it is preferably 0.1-10 wt %, more preferably 1-7 wt %, more preferably 3-5 wt % relative to the total amount of the oil-in-water emulsified composition.

"(G) Water"

In the present invention, water, together with other water based ingredients, is an ingredient that constitutes the water phase of the oil-in-water emulsified composition; it is preferable to use ion-exchanged water.

The blend ratio of water is determined as appropriate; it is preferably 50-90 wt %, more preferably 60-80 wt %, most preferably 65-75 wt % relative to the total amount of the oil-in-water emulsified composition.

In addition to the aforementioned essential ingredients, polyhydric alcohols and humectants can be blended into the oil-in-water emulsified composition of the present invention to improve the moisture retaining effect as long as the effect of the present invention is not adversely affected.

Examples of the polyhydric alcohol include: dihydric alcohols such as ethylene glycol, propylene glycol, trimethylene glycol, 1,2-butylene glycol, 1,3-butylene glycol, tetramethylene glycol, 2,3-butylene glycol, pentamethylene glycol, 2-butene-1,4-diol, hexylene glycol, and octylene glycol; trihydric alcohols such as glycerin, trimethylolpropane, and 1,2,6-hexanetriol; tetrahydric alcohols such as pentaerythritol; pentahydric alcohols such as xylitol; hexahydric alcohols such as sorbitol and mannitol; polyhydric alcohol copolymers such as diethylene glycol, dipropylene glycol, triethylene glycol, polypropylene glycol, triglycerin, tetraglycerin, and polyglycerin; dihydric alcohol alkyl ethers such as ethylene glycol monomethyl ether, ethylene glycol monoethyl ether, ethylene glycol monobutyl ether, ethylene glycol monophenyl ether, ethylene glycol monohexyl ether, ethylene glycol mono-2-methyl hexyl ether, ethylene glycol isoamyl ether, ethylene glycol benzyl ether, ethylene glycol isopropyl ether, ethylene glycol dimethylether, ethylene glycol diethyl ether, and ethylene glycol dibutyl ether; dihydric alcohol alkyl ethers such as diethylene glycol monomethyl ether, diethylene glycol monoethyl ether, diethylene glycol monobutyl ether, diethylene glycol dimethyl ether, diethylene glycol diethyl ether, diethylene glycol dibutyl ether, diethylene glycol methylethyl ether, triethylene glycol monomethyl ether, triethylene glycol monoethyl ether, propylene glycol monomethyl ether, propylene glycol monoethyl ether, propylene glycol monobutyl ether, propylene glycol monoisopropyl ether, dipropylene glycol methyl ether, dipropylene glycol ethyl ether, and dipropylene glycol butyl ether; dihydric alcohol ether esters such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, and propylene glycol monophenyl ether acetate; glycerin mono alkyl ethers such as chimyl alcohol, selachyl alcohol, and batyl alcohol; sugar alcohols such as sorbitol, maltitol, maltotriose, mannitol, sucrose, erythritol, glucose, fructose, starch amylolysis sugar, maltose, xylitose, and alcohol prepared by the reduction of starch amylolysis sugar; glysolid; tetrahydro furfuryl alcohol; POE-tetrahydro furfuryl alcohol; POP-butyl ether; POP/POE-butyl ether; methylpolyoxypropylene glycerin ether; POP-glycerin ether, POP-glycerin ether phosphoric acid; and POP/POE-pentane erythritol ether; any one, two or more of these are added.

Examples of the humectant include chondroitin sulfate, hyaluronic acid, mucoitin sulfate, charonic acid, atelocollagen, short chain soluble collagen, chestnut rose extract, and yarrow extract.

Various other ingredients that are usually used in cosmetics can be blended into the oil-in-water emulsified composition of the present invention. For example, powder ingredients, water-soluble polymers, thickeners, ultraviolet absorbents, sequestering agents, ethanol, pH adjusting agents, skin nutrients, antioxidants, antioxidation assistants, perfumes, and pigments can be blended in as necessary; and the composition can be prepared with a conventional high pressure emulsification method.

"Miniaturization of the Emulsified Particles by Means of High Pressure Emulsification"

The oil-in-water emulsified composition of the present invention is preferably prepared by means of high pressure emulsification of a mixed dispersion liquid containing the aforementioned essential ingredients using a high pressure homogenizer such as Manton Gualin, French press, and microfluidizer under a pressure of 30 MPa or higher. 50 MPa or more is more preferable.

The emulsified particles miniaturized by means of the high pressure emulsification of the present invention should preferably have an emulsified particle size of 0.03-0.15 micrometers.

The viscosity of the oil-in-water emulsified composition of the present invention should preferably be low; its physical properties should preferably be like an aqueous solution. The viscosity as measured by a B type viscometer (60 rpm, 1 min, 30° C.) should be preferably in the range of 5-50 (mPa·s).

The oil-in-water emulsified composition of the present invention can maintain a stable emulsified state even when a salt type drug is blended in and therefore it can be preferably used as a cosmetic containing a salt type drug, particularly a skin cosmetic.

EXAMPLES

The invention is described in detail through Examples below, but the invention shall not be limited to them. The blend ratios are in wt % (mass-percentage) units unless specified otherwise.

The oil-in-water emulsified compositions shown in the following tables were prepared by means of high pressure emulsification with a conventional method by using a high pressure homogenizer at a pressure of 55 MPa.

The obtained oil-in-water emulsified compositions were put into sample tubes and the external appearance right after the preparation was visually observed and evaluated based on the following criteria Next, for evaluation of stability over time, the external appearance was visually observed after four weeks of storage in a thermostatic tank at 50° C. and evaluated based in the following criteria. .

<Evaluation Criteria>
○: There is no change in the external appearance and the stability is excellent.
Δ: Aggregation and/or creaming is observed.
x: Gelation occurs.

TABLE 1

| | | Example 1 | Example 2 | Example 3 | Example 4 |
|---|---|---|---|---|---|
| (1) | (D) Stearic acid | 0.47 | 0.47 | 0.47 | 0.47 |
| (2) | (D) Behenic acid | 0.53 | 0.53 | 0.53 | 0.53 |
| (3) | (E) Stearyl alcohol | 0.28 | 0.28 | 0.28 | 0.28 |
| (4) | (E) Behenyl alcohol | 1.22 | 1.22 | 1.22 | 1.22 |
| (5) | (F) Methylpolysiloxane | 1 | 1 | 1 | 1 |
| (6) | (F) α-olefin oligomer | 4 | 4 | 4 | 4 |
| (7) | (G) Ion-exchanged water (1) | 15 | 15 | 15 | 15 |
| (8) | (C) Sodium N-stearoyl-L-glutamate | 0.3 | 0.3 | 0.3 | 0.3 |
| (9) | Glycerin | 8 | 8 | 8 | 8 |
| (10) | 1,3-butylene glycol | 4 | 4 | 4 | 4 |
| (11) | (D) Potassium hydroxide | 0.175 | 0.175 | 0.175 | 0.175 |
| (12) | (G) Ion-exchanged water (2) | Balance | Balance | Balance | Balance |
| (13) | (B) Polyoxyethylene cetyl ether (POE = 25) | 0.3 | 0.3 | 0.3 | 0.3 |
| (14) | (A) Potassium 4-methoxysalicylate | 3 | 1 | — | — |
| (15) | (A) L-ascorbic acid 2-glucoside | — | — | 2 | — |
| (16) | (A) Dipotasium glycyrrhizate | — | — | — | 0.5 |
| (17) | Ethanol | 2 | 2 | 2 | 2 |
| (18) | Disodium edetate | 0.01 | 0.01 | 0.01 | 0.01 |
| | External appearance right after preparation | ○ | ○ | ○ | ○ |
| | Stability over time (50° C., 4 W) | ○ | ○ | ○ | ○ |
| | Emulsified particle size (micrometers) (right after preparation) | 0.06 | 0.06 | 0.06 | 0.06 |
| | Emulsified particle size (micrometers) (50° C., 4 W) | 0.08 | 0.07 | 0.08 | 0.06 |

<Preparation Method>

(1)-(6) are stirred and mixed at 80° C. This is mixed with a mixed solution of (7)-(11) that is heated and dissolved at 70° C. while being stirred, and then emulsified using a high pressure homogenizer at a pressure of 55 MPa, which is mixed into a mixed solution of (12)-(16) while being stirred.

The results in "Table 1" show that the oil-in-water emulsified composition of the present invention is a very stable oil-in-water emulsified composition even when as much as 1-3 wt % of potassium 4-methoxysalicylate, which is an electrolyte salt type drug is blended in. It is also shown that a very stable oil-in-water emulsified composition is obtained when other salt type drugs, such as 2 wt % of L-ascorbic acid 2-glucoside or 0.5 wt % of glycyrrhizin, are blended in.

A cosmetic composed of the obtained oil-in-water emulsified composition has physical properties like an aqueous solution and, once applied on the skin, manifests a superior cream-like texture.

The size of the emulsified particles in Examples 1 and 2 is 0.05-0.1 micrometers, i.e. they are fine particles.

Oil-in-water emulsified compositions of the Comparative examples and their stability over time are shown below.

The oil-in-water emulsified compositions of Comparative examples were prepared following the preparation method of Examples 1 and 2.

TABLE 2

| | Comparative example 1 | Comparative example 2 | Comparative example 3 | Comparative example 4 | Comparative example 5 | Comparative example 6 | Comparative example 7 |
|---|---|---|---|---|---|---|---|
| (A) Potassium 4-methoxysalicylate | — | 1 | 2 | 3 | 1 | 2 | 3 |
| (C) Sodium N-stearoyl-L-glutamate | — | — | — | — | 0.3 | 0.3 | 0.3 |
| Glycerin | 8 | 8 | 8 | 8 | 8 | 8 | 8 |
| 1,3-butylene glycol | 4 | 4 | 4 | 4 | 4 | 4 | 4 |
| (D) Potassium hydroxide | 0.18 | 0.18 | 0.18 | 0.18 | 0.18 | 0.18 | 0.18 |
| (D) Stearic acid | 0.5 | 0.5 | 0.5 | 0.5 | 0.5 | 0.5 | 0.5 |
| (D) Behenic acid | 0.5 | 0.5 | 0.5 | 0.5 | 0.5 | 0.5 | 0.5 |
| Stearyl alcohol | 0.3 | 0.3 | 0.3 | 0.3 | 0.3 | 0.3 | 0.3 |
| (E) Behenyl alcohol | 1.2 | 1.2 | 1.2 | 1.2 | 1.2 | 1.2 | 1.2 |
| (F) Methylpolysiloxane | 1 | 1 | 1 | 1 | 1 | 1 | 1 |
| (F) α-olefin oligomer | 4 | 4 | 4 | 4 | 4 | 4 | 4 |
| Ethanol | 2 | 2 | 2 | 2 | 2 | 2 | 2 |
| Disodium edetate | 0.01 | 0.01 | 0.01 | 0.01 | 0.01 | 0.01 | 0.01 |
| (G) Ion-exchanged water | Balance | Balance | Balance | Balance | Balance | Balance | Balance |
| External appearance right after preparation | ○ | x | x | x | ○ | ○ | ○ |

TABLE 2-continued

|  | Comparative example 1 | Comparative example 2 | Comparative example 3 | Comparative example 4 | Comparative example 5 | Comparative example 6 | Comparative example 7 |
|---|---|---|---|---|---|---|---|
| Stability over time (50° C., 4 W) | ○ | x | x | x | Δ | Δ | Δ |
| Emulsified particle size (micrometers) (right after preparation) | 0.06 | — | — | — | 0.06 | 0.06 | 0.06 |
| Emulsified particle size (micrometers) (50° C., 4 W) | 0.06 | — | — | — | 0.09 | 0.11 | 0.18 |

Comparative example 1 does not contain (A) potassium 4-methoxysalicylate, which is a salt type drug, and therefore is stable over time with no problem.

However, Comparative examples 2-4, which contain a salt type drug (A) potassium 4-methoxysalicylate, do not contain (B) polyoxyethylene cetyl ether (POE=25) and (C) sodium N-stearoyl-L-glutamate; and gelation occurs right after the preparation.

On the other hand, Comparative examples 5-7 contain the (C) ingredient and therefore the stability over time improves a little compared with Comparative examples 2-4; but the (B) ingredient is not blended in and aggregation and/or creaming is observed over time, which is a problem in terms of a product's stability over time.

TABLE 3

|  | Comparative example 2 | Comparative example 8 | Comparative example 9 | Comparative example 10 | Comparative example 11 | Comparative example 12 | Comparative example 13 | Comparative example 14 | Comparative example 15 |
|---|---|---|---|---|---|---|---|---|---|
| (B) PEG-60 glyceryl isostearate |  | 0.5 |  |  |  |  |  |  |  |
| (B) POE (60) hydrogenated castor oil |  |  | 0.5 |  |  |  |  |  |  |
| (B) POE (100) hydrogenated castor oil |  |  |  | 0.5 |  |  |  |  |  |
| (B) PEG-40 stearate |  |  |  |  | 0.5 |  |  |  |  |
| (B) POE (25) cetyl ether |  |  |  |  |  | 0.5 |  | 0.5 | 0.5 |
| POE (30) behenyl ether |  |  |  |  |  |  | 0.5 |  |  |
| (A) Potassium 4-methoxy-salicylate | 1 | 1 | 1 | 1 | 1 | 1 | 1 | 2 | 3 |
| Glycerin | 8 | 8 | 8 | 8 | 8 | 8 | 8 | 8 | 8 |
| 1,3-butylene glycol | 4 | 4 | 4 | 4 | 4 | 4 | 4 | 4 | 4 |
| (D) Potassium hydroxide | 0.18 | 0.18 | 0.18 | 0.18 | 0.18 | 0.18 | 0.18 | 0.18 | 0.18 |
| (D) Stearic acid | 0.5 | 0.5 | 0.5 | 0.5 | 0.5 | 0.5 | 0.5 | 0.5 | 0.5 |
| (D) Behenic acid | 0.5 | 0.5 | 0.5 | 0.5 | 0.5 | 0.5 | 0.5 | 0.5 | 0.5 |
| (E) Stearyl alcohol | 0.3 | 0.3 | 0.3 | 0.3 | 0.3 | 0.3 | 0.3 | 0.3 | 0.3 |
| (E) Behenyl alcohol | 1.2 | 1.2 | 1.2 | 1.2 | 1.2 | 1.2 | 1.2 | 1.2 | 1.2 |
| (F) Methyl-polysiloxane | 1 | 1 | 1 | 1 | 1 | 1 | 1 | 1 | 1 |
| (F) α-olefin oligomer | 4 | 4 | 4 | 4 | 4 | 4 | 4 | 4 | 4 |
| Ethanol | 2 | 2 | 2 | 2 | 2 | 2 | 2 | 2 | 2 |
| Disodium edetate | 0.01 | 0.01 | 0.01 | 0.01 | 0.01 | 0.01 | 0.01 | 0.01 | 0.01 |
| (G) Ion-exchanged water | Balance | Balance | Balance | Balance | Balance | Balance | Balance | Balance | Balance |
| External appearance right after preparation | x | x | x | x | x | ○ | ○ | ○ | ○ |
| Stability over time (50° C., 4 W) | x | x | x | x | x | Δ | Δ | Δ | Δ |
| Emulsified particle size (micrometers) (right after preparation) | — | — | — | — | — | 0.06 | 0.06 | 0.06 | 0.06 |

TABLE 3-continued

|  | Comparative example 2 | Comparative example 8 | Comparative example 9 | Comparative example 10 | Comparative example 11 | Comparative example 12 | Comparative example 13 | Comparative example 14 | Comparative example 15 |
|---|---|---|---|---|---|---|---|---|---|
| Emulsified particle size (micrometers) (50° C., 4 W) | — | — | — | — | — | 0.18 | 0.22 | 0.22 | 0.34 |

Comparative example 2, and Comparative examples 8-15, which contain (A) potassium 4-methoxysalicylate, a salt type drug, do not contain (C) sodium N-stearoyl-L-glutamate and therefore there is a problem in terms of stability over time.

Comparative examples 12-15 contain a POE alkyl ether type nonionic surfactant and therefore the stability over time improves a little compared with Comparative example 2 and Comparative examples 8-11; but the (C) ingredient is not blended in and aggregation and/or creaming is observed over time, which is a problem in terms of a product's stability over time.

TABLE 4

|  | Comparative example 1 | Comparative example 7 | Comparative example 16 | Comparative example 17 |
|---|---|---|---|---|
| (D) Stearic acid | 0.5 | 0.5 | — | 1 |
| (D) Behenic acid | 0.5 | 0.5 | 1 | — |
| (D) Potassium hydroxide | 0.18 | 0.18 | 0.16 | 0.19 |
| (A) Potassium 4-methoxysalicylate | — | 3 | 3 | 3 |
| Glycerin | 8 | 8 | 8 | 8 |
| 1,3-butylene glycol | 4 | 4 | 4 | 4 |
| (C) Sodium N-stearoyl-L-glutamate | 0.3 | 0.3 | 0.3 | 0.3 |
| (E) Stearyl alcohol | 0.3 | 0.3 | 0.3 | 0.3 |
| (E) Behenyl alcohol | 1.2 | 1.2 | 1.2 | 1.2 |
| (F) Methylpolysiloxane | 1 | 1 | 1 | 1 |
| (F) α-olefin oligomer | 4 | 4 | 4 | 4 |
| Ethanol | 2 | 2 | 2 | 2 |
| Disodium edetate | 0.01 | 0.01 | 0.01 | 0.01 |
| (G) Ion-exchanged water | Balance | Balance | Balance | Balance |
| External appearance right after preparation | ○ | ○ | ○ | x |
| Stability over time (50° C., 4 W) | ○ | Δ | Δ | x |
| Emulsified particle size (micrometers) (right after preparation) | 0.06 | 0.06 | 0.08 | — |
| Emulsified particle size (micrometers) (50° C., 4 W) | 0.06 | 0.18 | 0.38 | — |

Comparative example 1 does not contain (A) potassium 4-methoxysalicylate, which is a salt type drug, and therefore is stable over time with no problem.

On the other hand, Comparative example 7, and Comparative examples 16-17, which contain (A) potassium 4-methoxysalicylate, a salt type drug, do not contain (B) polyoxyethylene cetyl ether (POE=25) and therefore there is a problem in terms of stability over time.

TABLE 5

|  | Comparative example 1 | Comparative example 4 | Comparative example 18 | Comparative example 7 | Comparative example 19 | Comparative example 20 | Comparative example 21 | Comparative example 15 | Example 1 | Example 2 |
|---|---|---|---|---|---|---|---|---|---|---|
| (C) Sodium N-stearoyl-L-glutamate | — | — | 0.1 | 0.3 | 0.5 | — | — | — | 0.3 | 0.3 |
| (B) Polyoxyethylene cetyl ether (POE = 25) (HLB = 15) | — | — | — | — | — | 0.1 | 0.3 | 0.5 | 0.3 | 0.3 |
| (A) Potassium 4-methoxysalicylate | — | 3 | 3 | 3 | 3 | 3 | 3 | 3 | 3 | 1 |
| Glycerin | 8 | 8 | 8 | 8 | 8 | 8 | 8 | 8 | 8 | 8 |
| 1,3-butylene glycol | 4 | 4 | 4 | 4 | 4 | 4 | 4 | 4 | 4 | 4 |
| (D) Potassium hydroxide | 0.18 | 0.18 | 0.18 | 0.18 | 0.18 | 0.18 | 0.18 | 0.18 | 0.18 | 0.18 |
| (D) Stearic acid | 0.5 | 0.5 | 0.5 | 0.5 | 0.5 | 0.5 | 0.5 | 0.5 | 0.5 | 0.5 |
| (D) Behenic acid | 0.5 | 0.5 | 0.5 | 0.5 | 0.5 | 0.5 | 0.5 | 0.5 | 0.5 | 0.5 |
| (E) Stearyl alcohol | 0.3 | 0.3 | 0.3 | 0.3 | 0.3 | 0.3 | 0.3 | 0.3 | 0.3 | 0.3 |
| (E) Behenyl alcohol | 1.2 | 1.2 | 1.2 | 1.2 | 1.2 | 1.2 | 1.2 | 1.2 | 1.2 | 1.2 |
| (F) Methylpolysiloxane | 1 | 1 | 1 | 1 | 1 | 1 | 1 | 1 | 1 | 1 |
| (F) α-olefin oligomer | 4 | 4 | 4 | 4 | 4 | 4 | 4 | 4 | 4 | 4 |

TABLE 5-continued

| | Comparative example 1 | Comparative example 4 | Comparative example 18 | Comparative example 7 | Comparative example 19 | Comparative example 20 | Comparative example 21 | Comparative example 15 | Example 1 | Example 2 |
|---|---|---|---|---|---|---|---|---|---|---|
| Ethanol | 2 | 2 | 2 | 2 | 2 | 2 | 2 | 2 | 2 | 2 |
| Disodium edetate | 0.01 | 0.01 | 0.01 | 0.01 | 0.01 | 0.01 | 0.01 | 0.01 | 0.01 | 0.01 |
| (G) Ion-exchanged water | Balance | Balance | Balance | Balance | Balance | Balance | Balance | Balance | Balance | Balance |
| External appearance right after preparation | ○ | x | x | ○ | ○ | x | ○ | ○ | ○ | ○ |
| Stability over time (50° C., 4 W) | ○ | x | x | Δ | Δ | x | Δ | Δ | ○ | ○ |
| Emulsified particle size (micrometers) (right after preparation) | 0.06 | — | — | 0.06 | 0.06 | — | 0.06 | 0.06 | 0.06 | 0.06 |
| Emulsified particle size (micrometers) (50° C., 4 W) | 0.06 | — | — | 0.18 | 0.12 | — | 0.45 | 0.34 | 0.08 | 0.07 |

Comparative example 1 does not contain (A) potassium 4-methoxysalicylate, which is a salt type drug, and therefore is stable over time with no problem. Comparative examples 7 and 18-19 do not contain the ingredient (B) polyoxyethylene cetyl ether (POE=25) and they have a problem in terms of stability over time. Comparative examples 15 and 21-21 do not contain the ingredient (C) sodium N-stearoyl-L-glutamate and they have a problem in terms of stability over time.

In contrast, Example 1 and Example 2 of the present invention contain the (B) and (C) ingredients and therefore there is no problem in terms of stability over time even when (A) potassium 4-methoxysalicylate, a salt type drug, is blended in.

INDUSTRIAL APPLICATIONS

The present invention can provide an oil-in-water emulsified composition prepared by miniaturizing emulsified particles by means of a high pressure emulsification method, said composition being superior in terms of emulsification stability such that salt type drugs can be stably blended in.

The oil-in-water emulsified composition of the present invention is preferably used for cosmetics containing salt type drugs.

The invention claimed is:

1. An oil-in-water emulsified composition comprising:
   1-3 wt % of potassium 4-methoxysalicylate or L-ascorbic acid-2-glucoside;
   hydrophilic nonionic surfactant;
   an N-long chain acyl acidic amino acid mono salt selected from the group consisting of sodium stearoyl glutamate, sodium lauroyl glutamate, potassium myristoyl glutamate, and sodium myristoyl glutamate;
   two or more types of higher fatty acids and alkali that constitutes a higher fatty acid soap;
   a higher alcohol selected from the group consisting of cetyl alcohol, stearyl alcohol, behenyl alcohol, myristyl alcohol, oleyl alcohol, cetostearyl alcohol, batyl alcohol, and isostearyl alcohol;
   oil component; and
   water;
   wherein the oil-in-water emulsified composition:
   is characterized by miniaturization of emulsified particles by means of high pressure emulsification under a pressure of 50 MPa or more down to an emulsified particle size range of 0.03-0.15 μm;
   has aqueous solution-like low viscosity physical properties; and
   has superior stability over time.

2. A cosmetic comprising the oil-in-water emulsified composition of claim 1.

3. The oil-in-water emulsified composition according to claim 1, wherein the hydrophilic nonionic surfactant is contained in an amount of 0.01-1 wt % relative to the total amount of the oil-in-water emulsified composition.

4. The oil-in-water emulsified composition according to claim 1, wherein the hydrophilic nonionic surfactant is contained in an amount of 0.2-0.5 wt % relative to the total amount of the oil-in-water emulsified composition.

5. The oil-in-water emulsified composition according to claim 1, wherein the hydrophilic nonionic surfactant is contained in an amount of 0.3-0.4 wt % relative to the total amount of the oil-in-water emulsified composition.

6. The oil-in-water emulsified composition according to claim 1, wherein the N-long chain acyl acidic amino acid mono salt is contained in an amount of 0.01-1 wt % relative to the total amount of the oil-in-water emulsified composition.

7. The oil-in-water emulsified composition according to claim 1, wherein the N-long chain acyl acidic amino acid mono salt is contained in an amount of 0.2-0.5 wt % relative to the total amount of the oil-in-water emulsified composition.

8. The oil-in-water emulsified composition according to claim 1, wherein the N-long chain acyl acidic amino acid mono salt is contained in an amount of 0.3-0.4 wt % relative to the total amount of the oil-in-water emulsified composition.

9. The oil-in-water emulsified composition according to claim 1, wherein the higher fatty acids, as a total of two or more types, are contained in an amount of 0.1-5 wt % relative to the total amount of the oil-in-water emulsified composition.

10. The oil-in-water emulsified composition according to claim 1, wherein the higher fatty acids, as a total of two or more types, are contained in an amount of 0.5-2 wt % relative to the total amount of the oil-in-water emulsified composition.

11. The oil-in-water emulsified composition according to claim 1, wherein the higher fatty acids, as a total of two or more types, are contained in an amount of 0.8-1.2 wt % relative to the total amount of the oil-in-water emulsified composition.

12. The oil-in-water emulsified composition according to claim 1, wherein the alkali is contained in an amount of 0.02-1.6 wt % relative to the total amount of the oil-in-water emulsified composition.

13. The oil-in-water emulsified composition according to claim 1, wherein the alkali is contained in an amount of 0.01-0.6 wt % relative to the total amount of the oil-in-water emulsified composition.

14. The oil-in-water emulsified composition according to claim 1, wherein the alkali is contained in an amount of 0.15-0.38 wt % relative to the total amount of the oil-in-water emulsified composition.

15. The oil-in-water emulsified composition according to claim 1, wherein the higher alcohol is contained in an amount of 0.1-5 wt % relative to the total amount of the oil-in-water emulsified composition.

16. The oil-in-water emulsified composition according to claim 1, wherein the higher alcohol is contained in an amount of 1-3 wt % relative to the total amount of the oil-in-water emulsified composition.

17. The oil-in-water emulsified composition according to claim 1, wherein the higher alcohol is contained in an amount of 1.5-2 wt % relative to the total amount of the oil-in-water emulsified composition.

18. The oil-in-water emulsified composition according to claim 1, wherein the oil component is contained in an amount of 0.1-10 wt % relative to the total amount of the oil-in-water emulsified composition.

19. The oil-in-water emulsified composition according to claim 1, wherein the oil component is contained in an amount of 1-7 wt % relative to the total amount of the oil-in-water emulsified composition.

20. The oil-in-water emulsified composition according to claim 1, wherein the oil component is contained in an amount of 3-5 wt % relative to the total amount of the oil-in-water emulsified composition.

21. A cosmetic comprising an oil-in-water emulsified composition, the oil-in-water emulsified composition comprising:
- 1-3 wt % of potassium 4-methoxysalicylate or L-ascorbic acid-2-glucoside;
- 0.01-1 wt % of hydrophilic nonionic surfactant;
- 0.01-1 wt % of an N-long chain acyl acidic amino acid mono salt selected from the group consisting of sodium stearoyl glutamate, sodium lauroyl glutamate, potassium myristoyl glutamate, and sodium myristoyl glutamate;
- 0.1-5 wt % of two or more types of higher fatty acids and 0.02-1.6 wt % of alkali that constitutes a higher fatty acid soap;
- 0.1-5 wt % of a higher alcohol selected from the group consisting of cetyl alcohol, stearyl alcohol, behenyl alcohol, myristyl alcohol, oleyl alcohol, cetostearyl alcohol, batyl alcohol, and isostearyl alcohol;
- 0.1-10 wt % of oil component; and
- 50-90 wt % of water;

wherein the wt % is relative to the total amount of the oil-in-water emulsified composition, and
wherein the oil-in-water emulsified composition:
- is characterized by miniaturization of emulsified particles by means of high pressure emulsification under a pressure of 50 MPa or more down to an emulsified particle size range of 0.03-0.15 µm;
- has aqueous solution-like low viscosity physical properties; and
- has superior stability over time.

* * * * *